United States Patent [19]

Geerlof et al.

[11] Patent Number: 5,182,209

[45] Date of Patent: Jan. 26, 1993

[54] ENANTIOSELECTIVE PREPARATION OF S-2R$_1$,2R$_2$-1,3-DIOXOLANE-4-METHANOL AND DERIVATIVES THEREOF

[75] Inventors: Arie Geerlof, Alphen a/d Rijn; Barend Groen, 's-Gravenhage; Johannis A. Duine, Schiedam, all of Netherlands

[73] Assignee: DSM N.V., Netherlands

[21] Appl. No.: 541,910

[22] Filed: Jun. 22, 1990

[30] Foreign Application Priority Data

Aug. 9, 1989 [NL] Netherlands ............... 8902035

[51] Int. Cl.$^5$ ............................................. C12P 41/00
[52] U.S. Cl. .................................. 435/280; 435/126; 435/253.3; 435/874; 435/252.1; 435/822
[58] Field of Search ............... 435/280, 126, 253.3, 435/252.1

[56] References Cited

U.S. PATENT DOCUMENTS 4,931,399 6/1990 Sih ........................................ 435/280
4,956,285 9/1990 De Smet .............................. 435/280

FOREIGN PATENT DOCUMENTS 0244912 11/1987 European Pat. Off. .

OTHER PUBLICATIONS

Adachi et al., "Purification and Characterization of Particulate Alcohol Dehydrogenase from Gluconobacter suboxydans", *Agric. Biol. Chem.*, 42 (11), (1978), pp. 2045–2056.

Jongejan et al., "Structural Properties of PQQ Involved in the Activity of Quinohaemoprotein Alcohol Dehydrogenase from Pseudomonas testosteroni". Eds. J. A. Jongejan and J. A. Duine, *PQQ and Quinoproteins*, Published by Kluwer Academic Publishers (1989), pp. 205–216.

Groen et al., "Quinohaemoprotein Alcohol Dehydrogenase Apoenzyme from Pseudomonas testosteroni", B. Chem. J., vol. 234, (1986), pp. 611–615.

Gu et al., "Bifunctional Chiral Synthons via Biochemical Methods—VIII: Optically-Active 3-Aroylthio-2-Methylpropionic Acids", *Tetrahedron Letters*, vol. 27, No. 43 (1986), pp. 5203–5206.

Chen et al., "Quantitative Analyses of Biochemical Kinetic Resolutions of Enantiomers", J. Am. Chem. Soc., vol. 104 (1982), pp. 7294–7299.

Jurczak et al., Tetrahedron Report Number 25. "(R)-And (S)-2,3-O-Isopropylideneglyceraldehyde in Stereo-selective Organic Synthesis", *Tetrahedron*, vol. 42, No. 2 (1986), pp. 447–488.

(List continued on next page.)

*Primary Examiner*—Carolyn Elmore

[57] ABSTRACT

Process for the enantioselective conversion of an enantiomer mixture of 2R$_1$,2R$_2$-1,3-dioxolane-4-methanol including the following steps: combining the enantioselective enzyme, PQQ-dependent alcohol dehydrogenase with an enantiomer mixture of 2R$_1$, 2R$_2$-1,3-dioxolane-4-methanol of the formula:

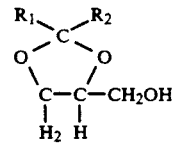

where R$_1$ and R$_2$ independently are selected from the group consisting of hydrogen, an optionally branched alkyl group, an aryl, and R$_1$ and R$_2$ with the carbon atom to which they are attached being an optionally substituted carbocyclic ring, the combination of ingredients producing 2R$_1$,2R$_2$-3-dioxolane-4-methanol enriched in the S-enantiomer i.e. S-2R$_1$,2R$_2$-1,3-dioxolane-4-methanol.

8 Claims, 1 Drawing Sheet

OTHER PUBLICATIONS

Tamaoka et al., "Reclassification of Pseudomonas acidovorans den Dooren de Jong 1926 and Pseudomonas testosteroni Marcus and Talalay 1956 as Comamonas acidovorans comb. nov. and Comamonas testosteroni comb. nov. with an Emended Description of the Genus Comamonas, Int'l. J. of Systematic Bacteriology," vol. 37, No. 1 (1987), pp 52–59.

Duine et al., "Isolation of a Methanol Dehydrogenase with a Functional Coupling to Cytochrome C", Short Communication, J. of General Microbiology, 115 (1979), 523–526.

Duine et al., "NAD-Dependent, PQQ-Containing Methanol Dehydrogenase: A Bacterial Dehydrogenase in a Multienzyme Complex," *FEBS Letters*, 168 (1984) 217–221.

J. A. Duine, "Review: Quinoproteins: enzymes containing the quinonoiid cofactor pyrroloquinoline quinone, topqquinone or tryptophan-tryptophan quinone", *Eur. J. Biochem.* (Feb. 1991), pp. 1–14.

Absorption (260 n m)

Time (min.)

ENANTIOSELECTIVE PREPARATION OF S-2$R_1$,2$R_2$-1,3-DIOXOLANE-4-METHANOL AND DERIVATIVES THEREOF

BACKGROUND AND SUMMARY OF THE INVENTION

This invention relates to a process for the enantioselective conversion of an enantiomer mixture of 2$R_1$, 2$R_2$-1,3-dioxolane-4-methanol of the formula:

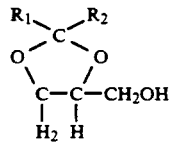

where $R_1$ and $R_2$ independently represent hydrogen or an optionally branched alkyl group, an aryl, or $R_1$ and $R_2$, together with the carbon atom to which they are attached, represent an optionally substituted carbocyclic ring, the product of said conversion being enriched in one of the enantiomers, which is achieved by subjecting this enantiomer mixture to the action of an enantioselective enzyme.

Such a process is known from EP-A-244,912. According to this published patent application, a product enriched in R-enantiomer can be obtained from an enantiomer mixture of an above-disclosed compound by subjecting such a mixture to the action of an enzyme that may originate from a great number of micro-organisms. According to the prior method it is mainly the S-enantiomer of the relevant compounds that is converted into the R-2$R_1$, 2$R_2$-1,3-dioxolane-4-carboxylic acid, so that a 2$R_1$, 2$R_2$-1,3-dioxolane-4-methanol enriched in R-enantiomer also remains. In said prior application it is also stated that the oxidation product, which contains an excess of R-2$R_1$, 2$R_2$-1,3-dioxolane-4-carboxylic acid, can be reduced to the corresponding alcohol, in which the amount of S-2$R_1$,2$R_2$-1,3-dioxolane-4-methanol is predominating.

For many applications, in particular for the use as starting compounds for the preparation of pharmaceutical compounds, it is desirable to have S-2$R_1$, 2$R_2$-1,3-dioxolane-4-methanol at one's disposal. For this purpose it is desirable to be able to prepare a product enriched in S-enantiomer directly from an enantiomer mixture of 2$R_1$, 2$R_2$-1,3-dioxolane-4-methanol. This can, for example, be achieved by means of an enantioselective enzymatic process.

DETAILED DESCRIPTION OF THE INVENTION

A process has now been found for the enantioselective conversion of an enantiomer mixture of 2$R_1$, 2$R_2$-1,3-dioxolane-4-methanol of the formula:

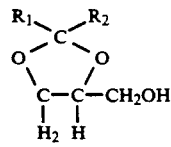

where $R_1$ and $R_2$ independently represent hydrogen or an optically branched alkyl group, an aryl, or $R_1$ and $R_2$, together with the carbon atom to which they are attached, represent an optionally substituted carbocyclic ring, the product of said conversion being enriched in one of the enantiomers, which is achieved by subjecting the enantiomer mixture to the action of an enantioselective enzyme by, and this characterizes the invention, preparing 2$R_1$, 2$R_2$-1,3-dioxolane-4-methanol enriched in S-enantiomer while applying a suitable pyrroloquinoline quinone (PQQ)-dependent alcohol dehydrogenase as enantioselective enzyme.

$R_1$, $R_2$ mostly represent H, or an $C_1$–$C_{10}$(cyclo) alkyl, a $C_5$–$C_{10}$, preferably $C_6$, aryl or $R_1$ and $R_2$ form together with the C-atom to which they are attached a carbocyclic ring with 4–10, preferably 5 or 6, C-atoms. $R_1$, $R_2$ and/or the carbocyclic ring they form together with the C-atom to which they are attached may be substituted with halogen atoms, lower alkyl ($C_1$–$C_4$) or lower alkoxy ($C_1$–$C_4$).

The so-called PQQ-dependent alcohol dehydrogenase to be used in the present invention is known in itself from, for instance, the dissertation "Quinoprotein (PQQ-containing) Alcohol Dehydrogenase" by J. A. Duine (PhD thesis, Delft, 19 Sep. 1985) and from B. W. Groen et al. in Biochem. J. 234 (1986) p. 611 ff. PQQ stands for pyrrolo-quinoline-quinone, i.e., 2,7,9-tricarboxy-1H-pyrrolo(2,3f)quinoline-4,5-dione. Suitable PQQ-dependent alcohol dehydrogenases are e.g. *Pseudomonas testosteroni* or *Gluconobacter suboxydans*. The PQQ-dependent alcohol dehydrogenase originating from or obtained from *Pseudomonas testosteroni* is eminently suitable for the subject process. The *Pseudomonas testosteroni* micro-organism can be cultured by the method described by B. W. Groen et al., loc., cit., but also by any other suitable cultivation method. Such cultivation methods are so commonly known and have been described so frequently in patent specifications and scientific publications as to render it superfluous to describe these cultivation methods in this context. The enzyme preparation as used in the subject invention is not restricted by purity and the like and may be both a crude enzyme solution and purified enzyme, but it may also consist of (permeabilized and/or immobilized) microbial cells that possess the desired activity, or of a homogenate of cells or whole cells possessing such activity. The enzyme may also be used in immobilized form or in chemically modified form. When some undesired opposite enzyme activity is present in the enzyme preparation used, it is recommended that this undesired activity be eliminated or be suppressed in order to obtain maximum enantioselectivity. The invention is in no way restricted by the form in which the enzyme for the subject invention is used. Within the scope of the invention use may also be made of a PQQ-dependent alcohol dehydrogenase originating from a mutant of *Pseudomonas testosteroni* or from genetically modified microorganisms. Preferably use is made of a PQQ-dependent alcohol dehydrogenase originating from or obtained from *Pseudomonas testosteroni* ATCC 15666, ATCC 15667, NCIB 8893, NCIB 8955 or NCIB 10808. According to Jin Tamaoko et al. in Int. J. Syst. Bact. 37 (1987) p. 52 ff, *Pseudomonas testosteroni* should be classified as *Comamonas testosteroni*. The organisms are referred to as *Pseudomonas testosteroni* in this application.

As is apparent from the publication by B. W. Groen et al. (loc. cit.), the PQQ-dependent alcohol dehydrogenase, such as can be obtained, for instance, from *Pseudomonas testosteroni*, is not active in all cases with regard to the oxidation of some alcohols: for activity a sufficient amount of PQQ must be present. If enough PQQ is not present in the cultivation of the microorganism, then it is desirable for oxidation purposes to add it in sufficient quantities. Instead of PQQ alone, PQQ analogues may also be used, such as monoesters of PQQ (at the 2-position), 4-hydroxy-PQ (PQ standing for pyrroloquinoline) or 5-hydroxy-PQ after oxidation, 3-methyl-PQQ, 3-ethyl-PQQ, 3-propyl-PQQ, N-methyl-PQQ, N-ethyl-PQQ, 8-methyl-PQQ or the PQQ-acetone adduct and other aldehyde and ketone adducts, as described by J. A. Jongejan, B. W. Groen and J. A. Duine in "PQQ and Quinoproteins" (J. A. Jongejans and J. A. Duine, eds.), Kluwer Academic Publishers, Dordrecht, 1989, pp. 205–216.

Enantioselective enzymatic conversions are known by themselves. The enantioselectivity resides in a difference in conversion rate between the enantiomers in question. Reaction products are obtained that are enriched in one of the enantiomers. For practical purposes it generally is desirable for one of the enantiomers to be obtained in a large excess. This is achieved by terminating the conversion at a certain degree of conversion. For enantioselective enzymatic hydrolyses this is described by Qu-Ming Gu et al. in Tetrahedron Letters 27 (1986), 5203 ff., and more in general by Ghing-Shih Chen et al. in J. Am. Chem. Soc. 104 (1982), 7294 ff. The general doctrine of enantioselective enzymatic conversions described in these publications also applies to the subject process.

According to the subject process the PQQ-dependent alcohol dehydrogenase oxidizes the R-enantiomer of $2R_1$, $2R_2$-1,3-dioxolane-4-methanol at a more rapid rate to form the S-enantiomer of the corresponding $2R_1$, $2R_2$-1,3-dioxolane-4-carboxylic acid, as a result of which a reaction product is obtained, enriched in S-$2R_1$, $2R_2$-1,3-dioxolane-4-methanol. The conversion rates of the enantiomers appear to differ considerably, as a result of which at 50% conversion of a racemic mixture an enantiomer excess of more than 90% of the $2R_1$, $2R_2$-1,3-dioxolane-4-methanol can be obtained, while an enantiomer excess of more than 95% can be reached at a conversion between 50 and 55%.

The range of starting proportion of PQQ dependent alcohol dehydrogenase relative to the enantiomer mixture is 1 mg–200 mg cells (dry weight) per g R,S-substrate.

Generally, the amount of PQQ is 0.5–2 equivalents with respect to the enzyme. For optimal results a minimum quantity of 1 equivalent is required.

The cells used in the reaction may be separated from the reaction mixture and reused in a subsequent conversion, without considerable loss of activity.

According to the subject process, preferably, the S-enantiomer is prepared from 2,2-dimethyl-1,3-dioxolane-4-methanol. An enantiomer excess of S-2,2-dimethyl-1,3-dioxolane-4-methanol of at least 95% can be obtained.

For example, in one embodiment of the present invention, conversion to S-2,2-dimethyl-1,3-dioxolane-4-methanol is by suspending 10–200 g of wet cells in 0.2–10.0 l potassium phosphate buffer and saturated with 0.5–60 μmol of PQQ to which is added 10–10.00 g R,S-2,2-dimethyl-1,3- dioxolane-4-methanol whereafter the solution is kept at 15°–50° C. temperature and 5–9 pH by titration for 6–72 hr amount of time.

This S-2,2-dimethyl-1,3-dioxolane-4-methanol is an important starting product for the preparation of pharmaceuticals, crop protection and/or agricultural pest control agents, as is also reported in a publication by J. Jurczak et al. in Tetrahedron 42 (1986) 447 ff. The R- and S-enantiomers of 2,2-dimethyl-1,3-dioxolane-4-methanol are important chiral $C_3$ synthons in organic synthesis. Examples of syntheses of more complex structures from such $C_3$ synthons are β-receptor blocking agents and sn-glycerylphosphoryl choline (GPC).

Racemic 2,2-dimethyl-1,3-dioxolane-4-methanol can be prepared in the way known for the preparation of acetals by acid-catalyzed coupling of glycerol and acetone. For compounds of the formula presented in the above, in which $R_1$ and $R_2$ do not both represent a methyl group, glycerol is to be coupled with the aldehyde or ketone in question.

BRIEF DESCRIPTION OF THE DRAWINGS

Further objects and advantages of the present invention will be understood by carefully reading the accompanying drawings, of which.

EXAMPLES

The invention will be further elucidated by the following examples, without being restricted by these examples. In these examples the analyses of the reaction products, notably with regard to the determination of the enantiomeric excess (ee), were performed using the method described below (TAGIT method). It is possible, if so desired, to calculate the selectivity value for the reaction with the aid of the formulae of Chen et al. (J. Am. Chem. Soc. 104, 7294 ff. (1982)). For conversion determination use was made of column separation over an Aminex HPX-87H HPLC column with 0.01N $H_2SO_4$ as mobile solvent and glycerol detection on the basis of the refractive index.

All analyses were always performed using samples taken, at different points of time, from the reaction mixtures of the experiments, the amounts being 10–50 ml for conversion determination and 10–50 ml for ee determination, depending on the conversion.

In ee determination the samples are extracted with two times 20 ml dichloromethane, after which 200 μl of the residue obtained after extract evaporation is dissolved in 5 ml diethylether. Subsequently 0.35 g tosylchloride and about 0.5 g potassium hydroxide powder are added to the ether solution, and the resulting solution is stirred at room temperature for 15 minutes. The tosyl addition product of the $2R_1$, $2R_2$-1,3-dioxolane-4-methanol is then isolated by extraction with diethylether and water, after which the ether fraction is washed with water and evaporated. The tosyl-$2R_1$, $2R_2$-1,3-dioxolane-4-methanol obtained is then dissolved in 2.0 ml n-butylamine and heated for 1 hour at 100° C. The reaction product is subsequently isolated by extraction with diethylether and water, after which the ether fraction is washed four times with water and evaporated. This residue is dissolved in 1.0 ml acetonitrile, after which 2.5 μl of the resulting solution is mixed with 50 μl acetonitrile and 1 mg 2,3,4,6-tetra-0-acetyl-β-glucopyranosyl-isothiocyanate (TAGIT). Five minutes after mixing, the ee is determined using a reversed phase ($C_{18}$) column with 60/40 methanol/water as eluent solvent.

Figure 1:
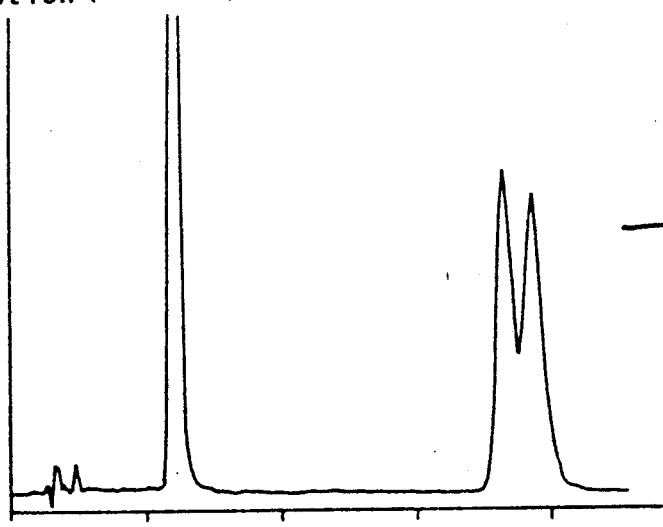
FIG. 1 is a specimen chromatograph for the racemate.
Figure 2:
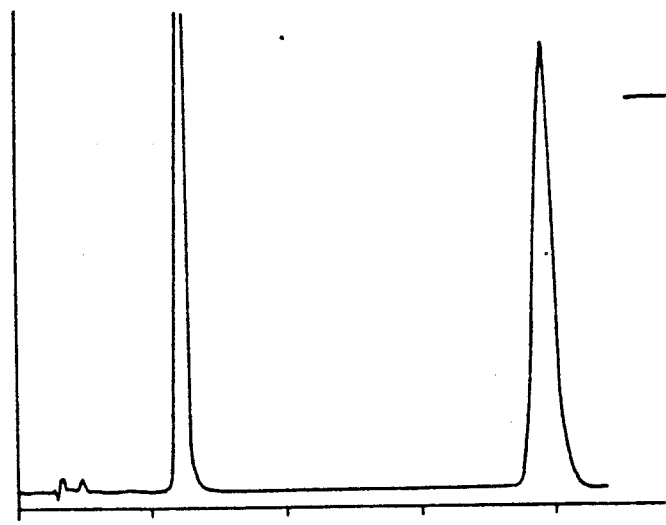
FIG. 2 is a specimen chromatograph for the commercially available S-enantiomer.
Figure 3:
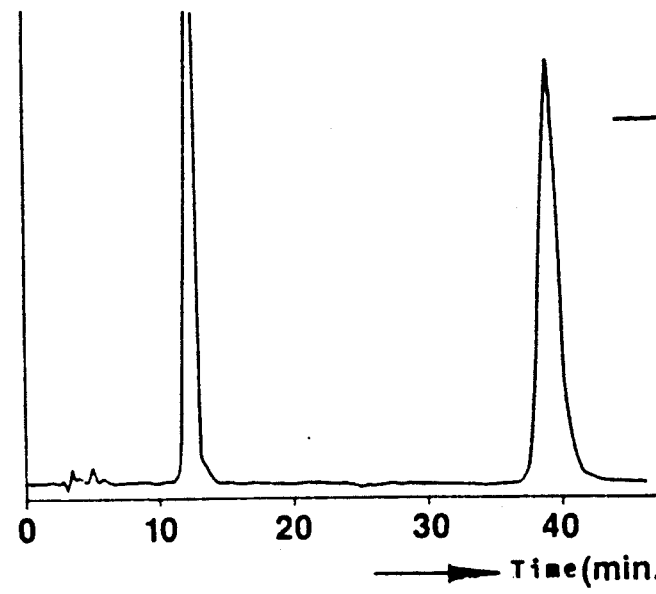
FIG. 3 is a specimen chromatograph for the product obtained according to the present invention after 56% conversion.

This method for determination of the enantiomer excess has been found to be very suitable. It gives an excellent separation of the R- and S-enantiomers of $2R_1$, $2R_2$-1,3-dioxolane-4-methanol (in derivatized form), as is illustrated in FIGS. 1, 2 and 3, which are added as specimen chromatograms of this separation. FIG. 1 relates to the racemate, for FIG. 2 use has been made of the commercially available S-enantiomer (Janssen Chimica), and FIG. 3 relates to the product obtained according to the invention after 56% conversion.

EXAMPLE I

*pseudomonas testosteroni* (American Type Culture Collection No. 15667) was cultured in a fermentor containing 20 l of mineral salts medium (composition per liter of demineralized water: 15.4 g $K_2HPO_4.3H_2O$, 4.52 g $KH_2PO_4$, 0.5 g $MgCl_2.6H_2O$, 3 g $(NH_4)_2SO_4$, 15 mg $CACl_2$, 15 mg $FeSO_4.7H_2O$ and the trace elements Cu, B, Mn, Zn, Mo), to which, after sterilization, 100 ml ethanol had been added. The pH was 7.0. The fermentor contents were kept at 28° C. and stirred at a speed of 350 rpm. The aeration rate was 3.5 l per minute. After 80 hours of cultivation the cells were harvested by centrifuging. A portion of these cells (wet weight 11 g) was suspended in 100 ml tris/HCl buffer (50 mM, pH 7.5), to which 5.3 μmol PQQ had been added. After the cells had been saturated with PQQ, 1.8 l of the same buffer and 20 g R,S-2 2-dimethyl-1,3-dioxolane-4-methanol were added. During incubation the cell suspension was aerated (1.0 l air per minute) and stirred (400 rpm), while the pH was kept at 7.5 by titration with 0.2N NaOH. The temperature was kept at 28° C.

During this oxidation, at regular intervals of four hours, samples were taken, which were analyzed in the way described above. Sampling occurred at 4 hr. (Sample 1), 8 hr. (Sample 2), 12 hr. (Sample 3) and 16 hr. (Sample 4). The results are summarized in Table 1. FIG. 3 refers to the results of this Example, for below Sample No. 4 at 56% conversion.

TABLE 1

| Sample | Conversion (%) | ee (S-enantiomer) (%) |
| --- | --- | --- |
| 1 | 15 | 17 |
| 2 | 32 | 45 |
| 3 | 45 | 75 |
| 4 | 56 | 99 |

Thus with respect to Sample 4, there was 56% conversion of 2,2-dimethyl-1,3-dioxolane-4-methanol and the enantiomeric excess (ee) of the S-enantiomer of 2,2-dimethyl-1,3-dioxolane-4-methanol was 99%.

EXAMPLE II

Using the purification method described in Biochem. J. (1986) 234, 611 ff., PQQ-dependent alcohol dehydrogenase was recovered from *Pseudomonas testosteroni* ATCC 15667, cultured as described in Example I. The isolated enzyme was dissolved in 20 ml potassium phosphate buffer (pH 8.0; 50 mM) and saturated with 100 nmol PQQ. Subsequently 1.01 mmol potassium ferricyanide and 0.5 mmol R,S-2,2-dimethyl-1,3-dioxolane-4-methanol were added. The pH of the solution was kept at 8.0 by titration with 0.1N NaOH. After reduction of ferricyanide the reaction mixture was analyzed. There was 51% conversion of 2,2-dimethyl-3-dioxolane-4-methanol yielding the S-2,2-dimethyl-1,3-dioxolane-4-methanol with ee value of 99%.

EXAMPLE III

The alcohol dehydrogenase recovered from *Pseudomonas testosteroni* ATCC 15667 (see Example II) was dissolved in 20 ml potassium phosphate buffer (pH 8.0; 50 mM) and saturated with 100 nmol PQQ, and subsequently excess potassium ferricyanide and 0.5 mmol 2,2-pentylene-1,3-dioxolane-4-methanol were added. After oxidation of about 50% of the substrate the reaction was stopped and the reaction mixture analyzed. Conversion appeared to be 54% and the enantiomer excess of the S-enantiomer was 99%.

EXAMPLE IV

Example III was repeated with 2,2-butylene-1,3-dioxolane-4-methanol instead of 2,2-pentylene-1,3-dioxolane-4-methanol. The conversion was 53% and the enantiomer excess of the S-enantiomer 99%.

EXAMPLE V

A 2.0 l Erlenmeyer flask, filled with 500 ml mineral salts medium (see Example I), 2.5 ml ethanol and 2 μmol PQQ, was inoculated with *Pseudomonas testosteroni* ATCC 15667. Both PQQ (filter sterilized) and ethanol had been added after sterilization by heating of the medium. The cultivation temperature was 28° C., and shaking took place at 200 rpm. After 36 hours the cells were harvested by centrifuging, after which they were suspended in 100 ml potassium phosphate buffer (pH 7.0; 50 mM). After addition of 1.0 g R,S-2,2-dimethyl-1,3-dioxolane-4-methanol, the reaction medium was incubated at 28° C. while being shaken (200 rpm). After 24 hours the reaction medium was analyzed. Conversion was 54%, and the ee value for the S-enantiomer 96%.

EXAMPLE VI

Using the method of Example V, *Pseudomonas testosteroni* ATCC 15666, NCIB 8893 and NCIB 10808 were respectively cultured, and each time the PQQ-dependent alcohol dehydrogenase obtained was used for enantiospecific oxidation of R,S-2,2-dimethyl-1,3-dioxolane-4-methanol as described in example IV, with similar results as regards the enantioselectivity.

EXAMPLE VII

Using the purification method described in Agric. Biol. Chem. 42 (1978) 2045-2056, purified, membrane bound, PQQ-dependent alcohol dehydrogenase recovered from *Gluconobacter suboxydans* ATCC 621, was dissolved in 20 ml potassium phosphate buffer (pH=7.0; 50 mM) and saturated with 100 nmol PQQ. Subsequently excess potassium ferricyanide and 0.5 mmol R,S-2,2-dimethyl-1,3-dioxolane-4-methanol were added. After oxidation of about 60% of the substrate, the reaction was stopped. There was 64% conversion to S-2,2-dimethyl-1,3-dioxolane-4-methanol with an enantiomeric excess of 96%.

EXAMPLE VIII

*Pseudomonas testosteroni* ATCC 15667 was cultured in a fermentor containing 5 l of a medium containing mineral salts as described in Example I (pH =7), to which, after sterilization, 25 ml ethanol, as a carbon source, was added. At the end of the exponential growth phase, the pH was increased to 7.5. Subsequently 150 mmol R,S-2,2-dimethyl-1,3-dioxolane-4-methanol and 2.5 mg PQQ were added while the pH was kept at 7.5 by titration with 0.2N NaOH. After oxidation of 57% of the substrate added, the cells were separated off with a centrifuge, and the remaining substrate was isolated by extraction. The enantiomer excess of the S-enantiomer of 2,2-dimethyl-1,3-dioxolane-4-methanol dioxolane was $\geq 99.5\%$.

EXAMPLE IX

The cells remaining from example VIII were reused. To this end the cells were suspended in 1.0 l tris/HCl buffer (50 mM, pH 7.5), to which 20 g R,S-2,2-dimethyl-1,3-dioxolane-4-methanol were added. After oxidation of 54% of the racemate (54% conversion), the S-enantiomer of R,S-2,2-dimethyl-1,3-dioxolane-4-methanol remained with an enantiomeric excess of 97%.

While only a few exemplary embodiments of this invention have been described in detail, those skilled in the art will recognize that there are many possible variations and modifications which may be made in the exemplary embodiments while yet retaining many of the novel and advantageous features of this invention. Accordingly, it is intended that the following claims cover all such modifications and variations.

What is claimed is:

1. Process for the enantioselective conversion of an enantiomer mixture of $2R_1$, $2R_2$-1,3-dioxolane-4-methanol comprising the following steps:

combining the enantioselective enzyme, PQQ-dependent alcohol dehydrogenase with an enantiomer mixture of $2R_1$, $2R_2$-1,3-dioxolane-4-methanol of the formula:

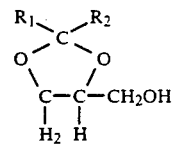

where $R_1$ and $R_2$ independently are selected from the group consisting of hydrogen, an optionally branched alkyl group, an aryl, and $R_1$ and $R_2$ with the carbon atom to which they are attached being an optionally substituted carbocyclic ring, said combination of ingredients producing $2R_1$, $2R_2$-3-dioxolane-4-methanol enriched in $S-2R_1$, $2R_2$-1,3-dioxolane-4-methanol.

2. Process according to claim 1, wherein said $S-2R_1$, $2R_2$-1,3-dioxolane-4-methanol is prepared with an enantiomer excess of at least 95%.

3. Process according to claim 1 wherein 2,2-dimethyl-1,3-dioxolane-4-methanol enriched in S-enantiomer is prepared.

4. Process according to claim 1, wherein said PQQ-dependent alcohol dehydrogenase is obtained from *Pseudomonas testosteroni*.

5. Process according to claim 4, wherein said PQQ-dependent alcohol dehydrogenase is obtained from *Pseudomonas testosteroni* ATCC 15666, ATCC 15667, NCIB 8893, NCIB 8955 or NCIB 10808.

6. Process according to claim 1, wherein said PQQ-dependent alcohol dehydrogenase is obtained from *Gluconobacter suboxydans*.

7. Process according to claim 6, wherein said PQQ-dependent alcohol dehydrogenase is obtained from *Gluconobacter suboxydans* ATCC 621.

8. Process according to claim 1 wherein said PQQ-dependent alcohol dehydrogenase originates from microbial cells of the genera *Pseudomonas* or *Gluconobacter* 10-200 g of said cells being suspended in 0.2-10.0 l potassium phosphate buffer and saturated with 0.5-60 μmol of PQQ to which is added 10-10.00 g R,S-2,2-dimethyl-1,3-dioxolane-4-methanol whereafter the solution is kept at 15°-50° C. temperature and 5-9 pH by titration for 6-72 hr amount of time.

* * * * *